(12) United States Patent
Aoyama

(10) Patent No.: US 11,308,578 B2
(45) Date of Patent: Apr. 19, 2022

(54) ENDOSCOPE SYSTEM

(71) Applicant: FUJIFILM Corporation, Tokyo (JP)

(72) Inventor: Tatsuya Aoyama, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 17/022,541

(22) Filed: Sep. 16, 2020

(65) Prior Publication Data

US 2020/0410639 A1    Dec. 31, 2020

Related U.S. Application Data

(63) Continuation of application No. PCT/JP2019/014684, filed on Apr. 2, 2019.

(30) Foreign Application Priority Data

Apr. 11, 2018   (JP) ............... JP2018-076061

(51) Int. Cl.
*G06T 3/40* (2006.01)
*H04N 9/04* (2006.01)
*A61B 1/05* (2006.01)
*A61B 1/06* (2006.01)
*H04N 5/225* (2006.01)

(52) U.S. Cl.
CPC .............. *G06T 3/4015* (2013.01); *A61B 1/05* (2013.01); *A61B 1/063* (2013.01); *A61B 1/0638* (2013.01); *H04N 5/2256* (2013.01); *H04N 9/04555* (2018.08); *H04N 9/04557* (2018.08); *H04N 2005/2255* (2013.01); *H04N 2209/046* (2013.01)

(58) Field of Classification Search
CPC .................................. G06T 3/4015

USPC .......................................... 348/68
See application file for complete search history.

(56) References Cited

U.S. PATENT DOCUMENTS

| 2011/0176730 A1* | 7/2011 | Sasaki .................. G06T 3/4015 382/167 |
| 2015/0092034 A1 | 4/2015 | Iwane |
| 2015/0272422 A1 | 10/2015 | Aoyama |

FOREIGN PATENT DOCUMENTS

| JP | 2000115793 A | 4/2000 |
| JP | 2009284931 A | 12/2009 |

(Continued)

OTHER PUBLICATIONS

International Search Report issued in PCT/JP2019/014684; dated Jul. 2, 2019.

(Continued)

*Primary Examiner* — Jeffery A Williams
(74) *Attorney, Agent, or Firm* — Studebaker & Brackett PC

(57) ABSTRACT

There is provided an endoscope system that can obtain a high-resolution endoscopic image not subjected to demosaicing processing as necessary. The endoscope system includes a light source unit that emits illumination light, an image sensor that includes a color filter having one color for each pixel among color filters having a plurality of colors and picks up an image of a subject using the illumination light, a demosaicing processing section that performs demosaicing processing on RAW images having the respective colors and corresponding to the color filters having the respective colors, and a switching section that switches whether to perform the demosaicing processing using spectral information of the illumination light.

20 Claims, 15 Drawing Sheets

(56) References Cited

FOREIGN PATENT DOCUMENTS

| JP | 2009284959 A | 12/2009 |
|----|--------------|---------|
| JP | 201566063 A | 4/2015 |
| JP | 2015195844 A | 11/2015 |
| JP | 2017158840 A | 9/2017 |

OTHER PUBLICATIONS

International Preliminary Report On Patentability and Written Opinion issued in PCT/JP2019/014684; dated Oct. 13, 2020.
An Office Action; "Notice of Reasons for Refusal", mailed by the Japanese Patent Office dated Jun. 22, 2021, which corresponds to Japanese Patent Application No. 2020-513212 and is related to U.S. Appl. No. 17/022,541; with English language translation.

* cited by examiner

ENDOSCOPE SYSTEM

CROSS-REFERENCE TO RELATED APPLICATIONS

This application is a Continuation of PCT International Application No. PCT/JP2019/014684 filed on Apr. 2, 2019, which claims priority under 35 U.S.C § 119(a) to Japanese Patent Application No. 2018-076061 filed on Apr. 11, 2018. Each of the above application(s) is hereby expressly incorporated by reference, in its entirety, into the present application.

BACKGROUND OF THE INVENTION

1. Field of the Invention

The invention relates to an endoscope system that picks up the image of a subject through color filters.

2. Description of the Related Art

An endoscope system comprising a light source device, an endoscope, and a processor device has been spread in a medical field. The light source device generates illumination light. The endoscope picks up the image of a subject using an image sensor. The processor device performs processing and the like on the picked-up image of the subject.

In a case where an image sensor including a color filter having one color for each pixel among color filters having a plurality of colors is used, an original image (so-called RAW image) obtained from the image sensor has only information of any one channel of, for example, a red color (R), a green color (G), or a blue color (B) for each pixel. For this reason, demosaicing processing (which may be referred to as demosaicing) is performed on the RAW image. The RAW image is an image that is not yet subjected to demosaicing processing.

In a case where, for example, an image sensor including color filters having R, G, B, and W (white) colors for the respective pixels is used in the endoscope system, a method including regarding a W-pixel including a W color filter as a G-pixel including a G color filter or a B-pixel including a B color filter and performing mosaicing processing is known (JP2015-195844A).

Further, an endoscope system that switches the contents of demosaicing processing to a case where an image, which is displayed on a monitor or the like and is used for the observation of a subject, is generated and a case where numerical information about colors is acquired is known (JP2017-158840A). Specifically, in a case where numerical information about colors is acquired, the processing is switched from normal demosaicing processing to low-resolution demosaicing processing where color information is correct.

SUMMARY OF THE INVENTION

A tissue, such as a thin blood vessel, and/or a fine structure, such as a pit pattern, is an important diagnostic material in a diagnosis using an endoscope system. For this reason, it is preferable that the resolution of an image for display or the like is high in the endoscope system.

However, a plurality of processing algorithms for demosaicing processing are known, but all the processing algorithms supply data by interpolation. For this reason, the resolution of an image subjected to demosaicing processing degrades as compared to that of the RAW image.

An object of the invention is to provide an endoscope system that can obtain a high-resolution endoscopic image not subjected to demosaicing processing as necessary.

An endoscope system according to an aspect of the invention comprises a light source unit that emits illumination light, an image sensor that includes a color filter having one color for each pixel among color filters having a plurality of colors and picks up an image of a subject using the illumination light, a demosaicing processing section that performs demosaicing processing on RAW images having the respective colors and corresponding to the color filters having the respective colors and a switching section that switches whether to perform the demosaicing processing using spectral information of the illumination light.

It is preferable that the endoscope system further comprises a complementary processing section performing complementary processing for complementing a pixel value of a missing pixel of a specific color image, which is one of the RAW images having the respective colors and corresponding to the color filters having the respective colors, using a non-specific color image which is a RAW image different from the specific color image and the switching section switches processing to be performed between the demosaicing processing and the complementary processing.

It is preferable that the endoscope system further comprises a complementary processing section performing complementary processing for complementing a pixel value of a missing pixel of a specific color image, which is one of the RAW images having the respective colors and corresponding to the color filters having the respective colors, using a non-specific color image which is a RAW image different from the specific color image and the switching section switches processing to be performed to the complementary processing in a case where the illumination light is at least one of monochromatic light or narrow-band light corresponding to the color filters having the respective colors as the spectral information.

It is preferable that the complementary processing section complements the pixel value of the missing pixel of the specific color image using pixel values of the non-specific color image multiplied by gains.

It is preferable that the gains are parameters of calculation for causing the pixel values of the non-specific color image to be close to pixel values of the specific color image in a case where an image of a white subject is picked up.

It is preferable that the gains are coefficients for causing received light spectra of pixels forming pixel values of the specific color image and received light spectra of pixels forming the pixel values of the non-specific color image to be close to each other in a first received light spectrum obtained from spectral information of the illumination light and spectral transmittance of the color filters.

It is preferable that the gains are coefficients for causing received light spectra of pixels forming pixel values of the specific color image and received light spectra of pixels forming the pixel values of the non-specific color image to be close to each other in a second received light spectrum obtained from spectral information of the illumination light, spectral transmittance of the color filters, and spectral characteristics of the subject.

It is preferable that the endoscope system further comprises a storage unit storing the gains for each portion of the subject and the complementary processing section switches the gains to be used for each portion of the subject on the basis of the gains stored in the storage unit.

It is preferable that the illumination light is narrow-band light.

It is preferable that the narrow-band light is at least one of violet light, blue light, or green light.

It is preferable that the endoscope system further comprises a color image generation section generating a color image using a complemented image.

According to the endoscope system of the aspect of the invention, it is possible to obtain a high-resolution endoscopic image not subjected to demosaicing processing as necessary.

DESCRIPTION OF THE PREFERRED EMBODIMENTS

First Embodiment

Figure 1:
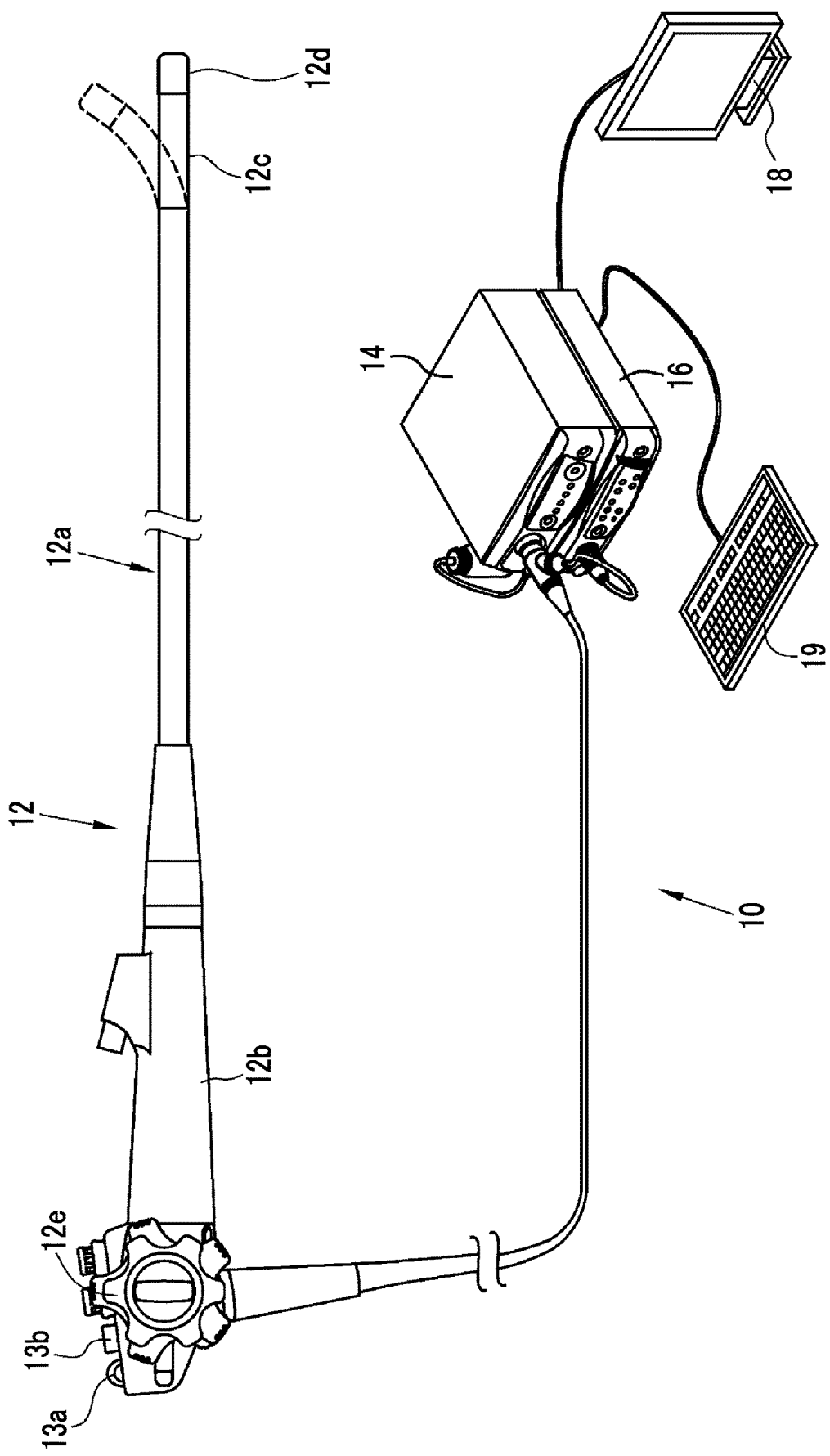
FIG. 1 is a diagram showing the appearance of an endoscope system.

As shown in FIG. 1, an endoscope system 10 (endoscope apparatus) comprises an endoscope 12, a light source device 14, a processor device 16, a monitor 18, and a console 19. The endoscope 12 picks up the image of a subject. The light source device 14 generates illumination light. The processor device 16 performs the control of the endoscope system 10, image processing, and the like. The monitor 18 is a display unit displaying the image that is picked up by the endoscope 12, and the like. The console 19 is an input device that is used to perform setting input and the like for the processor device 16 and the like.

The endoscope 12 includes an insertion part 12a that is to be inserted into an object to be examined, an operation part 12b that is provided at the proximal end portion of the insertion part 12a, and a bendable part 12c and a distal end part 12d that are provided on the distal end side of the insertion part 12a. The bendable part 12c is bent by the operation of angle knobs 12e of the operation part 12b. As a result, the distal end part 12d faces in a desired direction. Further, the operation part 12b is provided with a zoom operation part 13a and a mode switching operation part 13b in addition to the angle knobs 12e. The image of the subject can be picked up while being increased or reduced in size by the operation of the zoom operation part 13a. Furthermore, an observation mode is switched by the operation of the mode switching operation part 13b.

The observation mode is a combination of the type of illumination light used during image pickup, the contents of image processing performed in a case where an image for display or the like is generated, whether or not biological information, such as oxygen saturation, is calculated, the display mode of an image or the like, and conditions according to other observation. The endoscope system 10 has, for example, a normal observation mode where the image of a subject is picked up using white light and the subject is displayed in a natural tone, and a special observation mode where the image of a subject is picked up using illumination light having a specific wavelength range different from the wavelength range of white light and the subject is displayed.

Figure 2:
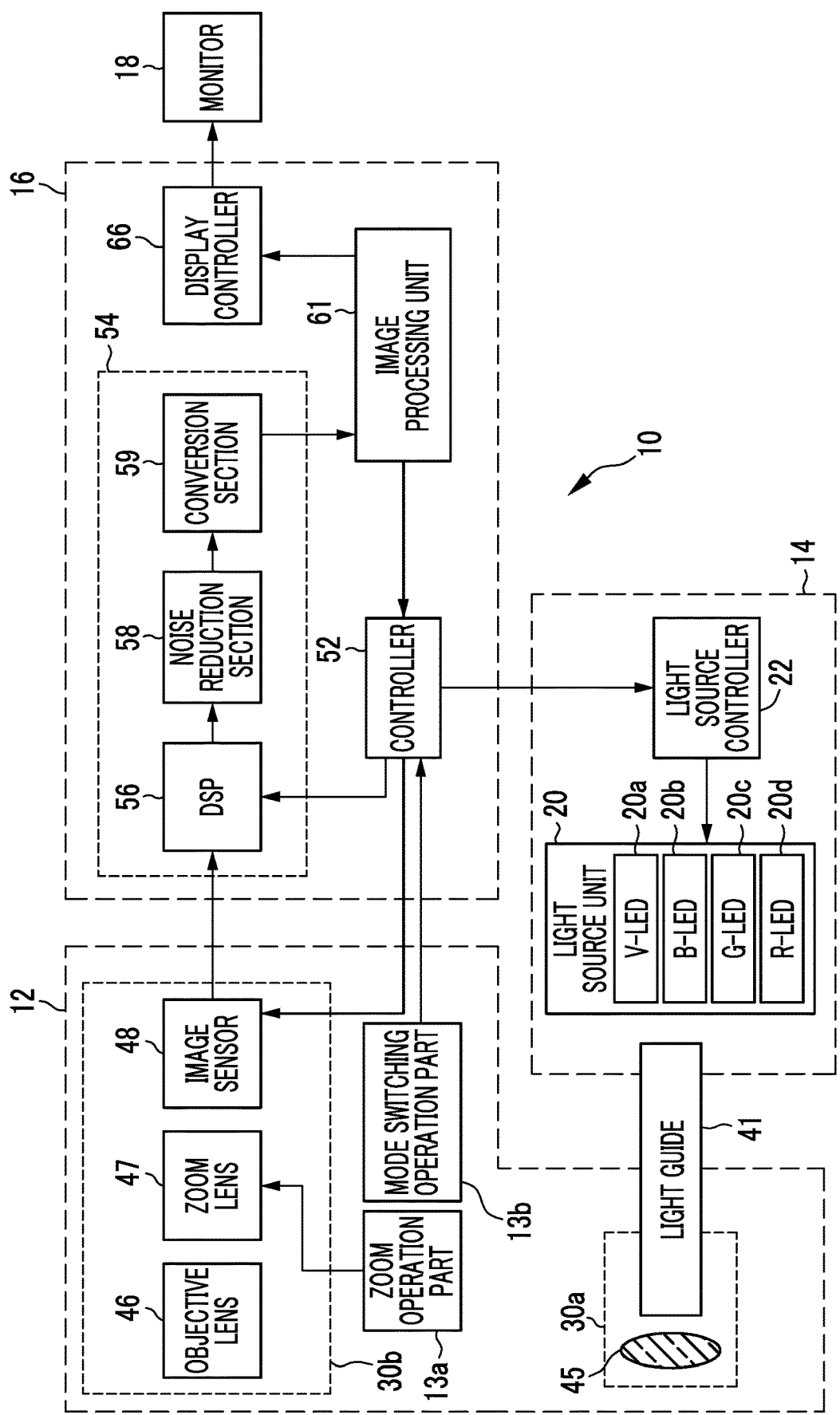
FIG. 2 is a block diagram of the endoscope system.

As shown in FIG. 2, the light source device 14 comprises a light source unit 20 that emits illumination light, and a light source controller 22 that controls the operation of the light source unit 20.

The light source unit 20 emits illumination light that is used to illuminate the subject. The emission of illumination light includes the emission of excitation light that is used to emit illumination light, and the like. For example, the light source unit 20 includes a light source, such as a laser diode (hereinafter referred to as LD), a light emitting diode (LED), a xenon lamp, or a halogen lamp; and emits at least white illumination light or excitation light that is used to emit white illumination light. White includes so-called pseudo white that is substantially equivalent to white in the image pickup of a subject using the endoscope 12. As necessary, the light source unit 20 includes: a fluorescent body that receives applied excitation light and emits light; an optical filter that adjusts the wavelength range, the spectrum, the amount of illumination light or excitation light, or the like; and the like. In addition, the light source unit 20 can emit light that has a specific wavelength range and is required to pick up an image used for the calculation of biological information, such as the oxygen saturation of hemoglobin included in a subject.

Figure 3:
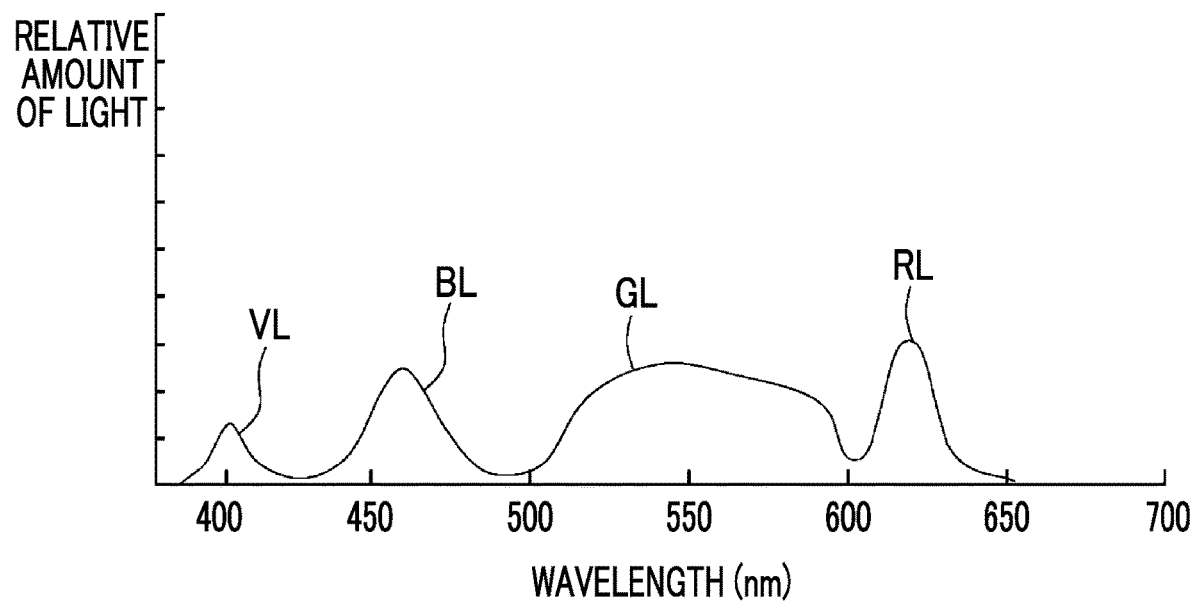
FIG. 3 is a graph showing the spectrum of illumination light.

In this embodiment, the light source unit 20 includes four color LEDs, that is, a V-LED 20*a*, a B-LED 20*b*, a G-LED 20*c*, and an R-LED 20*d*. As shown in FIG. 3, the V-LED 20*a* emits violet light VL of which the central wavelength is 405 nm and the wavelength range is in the range of 380 to 420 nm. The B-LED 20*b* emits blue light BL of which the central wavelength is 460 nm and the wavelength range is in the range of 420 to 500 nm. The G-LED 20*c* emits green light GL of which the wavelength range is in the range of 480 to 600 nm. The R-LED 20*d* emits red light RL of which the central wavelength is in the range of 620 to 630 nm and the wavelength range is in the range of 600 to 650 nm. The central wavelength of each of the V-LED 20*a* and the B-LED 20*b* has a width of about ±20 nm, preferably a width in the range of about ±5 nm to about ±10 nm.

Figure 4:
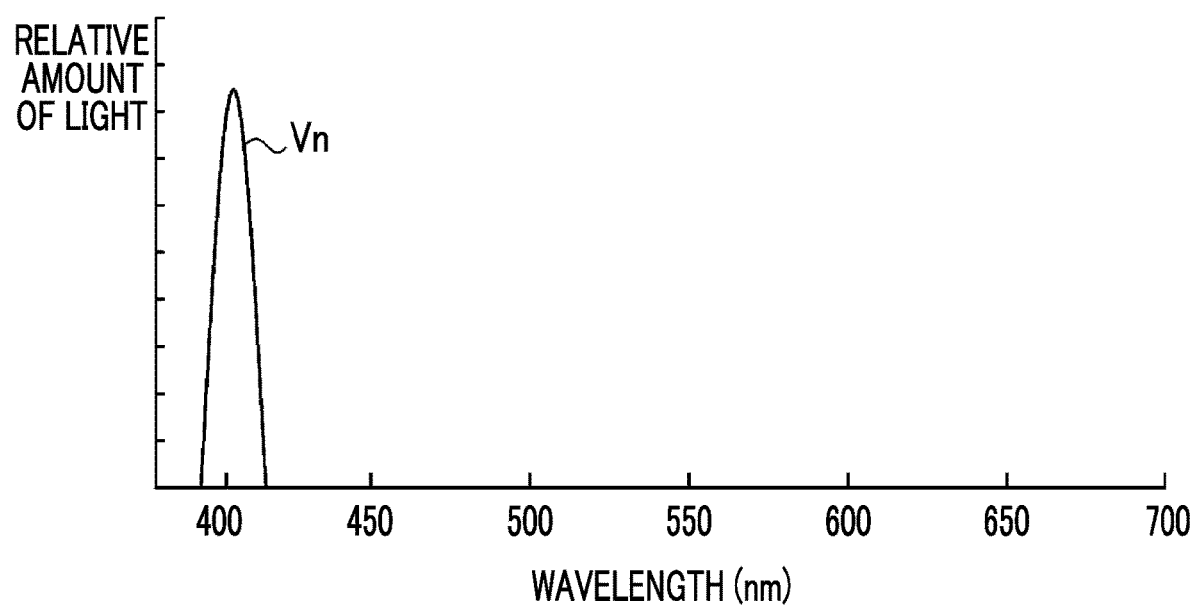
FIG. 4 is a graph showing the spectrum of narrow-band violet light.

The light source controller 22 controls a timing when each light source of the light source unit 20 is to be turned on or turned off or is to be shielded, the amount of light emitted from each light source, and the like. As a result, the light source unit 20 can emit various types of illumination light having different spectra. In this embodiment, the light source controller 22 controls the turn-on or turn-off of the respective LEDs 20*a* to 20*d*, the amount of light emitted from each LED during the turn-on, the insertion and removal of the optical filter, and the like by the input of independent control signals and adjusts the spectrum of illumination light. Accordingly, the light source unit 20 emits white light in the normal observation mode. Further, the light source unit 20 emits illumination light formed of at least violet light having a narrow band (hereinafter referred to as narrow-band violet light Vn) in the special observation mode as shown in FIG. 4. The "narrow band (narrow-band)" means a substantially single wavelength range in a relationship between the characteristics of a subject and/or the spectral characteristics of color filters of an image sensor 48. For example, in a case where the wavelength range of light is in the range of, for example, about ±20 nm or less (preferably about ±10 nm or less) from the central wavelength of the light, it is regarded that this light has a narrow band.

The distal end part 12*d* of the endoscope 12 is provided with an illumination optical system 30*a* and an image pickup optical system 30*b*. The illumination optical system 30*a* includes an illumination lens 45 and illumination light is emitted to a subject through the illumination lens 45.

The image pickup optical system 30*b* includes an objective lens 46, a zoom lens 47, and an image sensor 48. The image sensor 48 picks up the image of a subject using the reflected light and the like (including scattered light, fluorescence emitted from the subject, fluorescence caused by a medicine given to the subject, or the like in addition to the reflected light) of illumination light returning from the subject through the objective lens 46 and the zoom lens 47. The zoom lens 47 is moved by the operation of the zoom operation part 13*a* and increases or reduces the size of a subject image.

Figure 5:
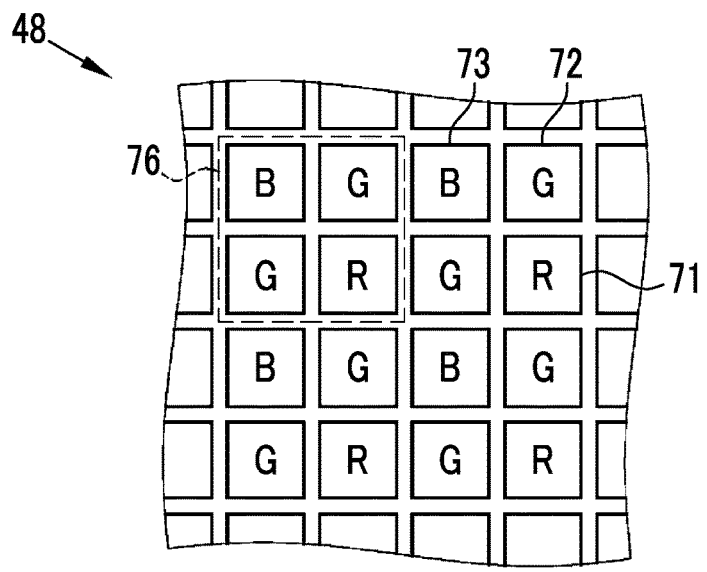
FIG. 5 is a diagram illustrating the arrangement of color filters of an image sensor.

As shown in FIG. 5, the image sensor 48 includes a color filter having one color for each pixel among color filters having a plurality of colors. In this embodiment, the image sensor 48 is a color sensor including primary color filters. Specifically, the image sensor 48 includes R-pixels 71 that include red color filters R (hereinafter referred to as R-fil-ters), G-pixels 72 that include green color filters G (hereinafter referred to as G-filters), and B-pixels 73 that include blue color filters B (hereinafter referred to as B-filters). Further, in this embodiment, the arrangement of the pixels having the respective colors is so-called Bayer arrangement as shown in FIG. 5.

Figure 6:
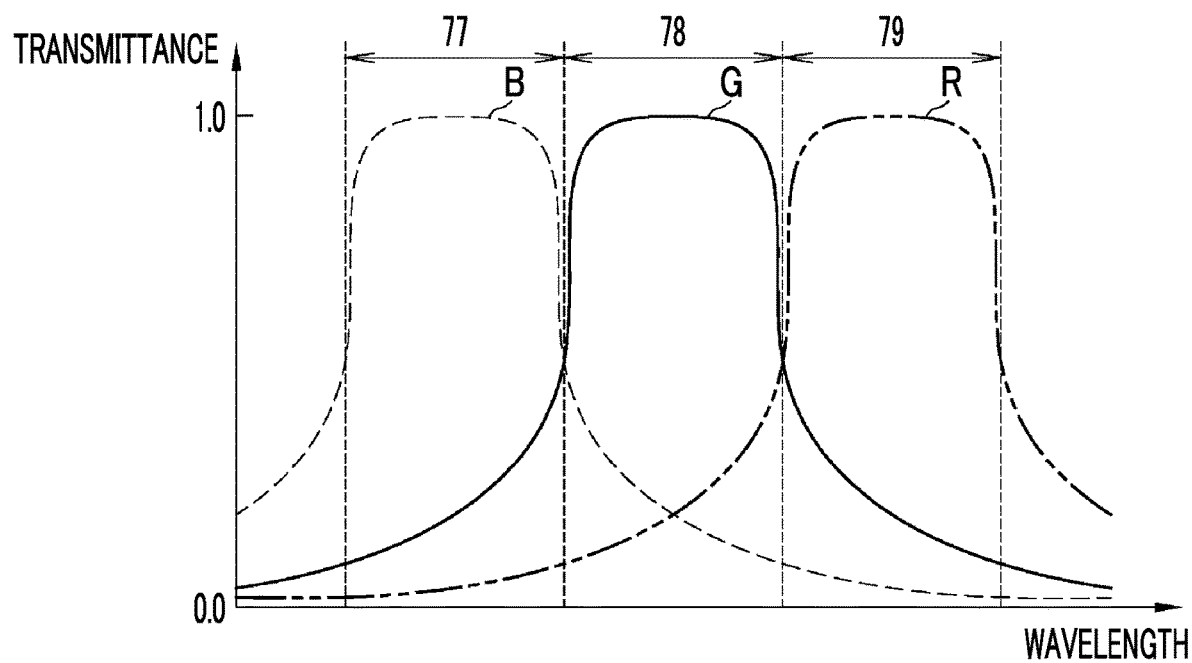
FIG. 6 is a graph of the spectral characteristics of the color filters.

As shown in FIG. 6, the B-filter transmits light having a short-wavelength range 77. For example, blue light to violet light belongs to the short-wavelength range 77. Accordingly, the reflected light and the like of the violet light VL, the narrow-band violet light Vn, and the blue light BL from the subject are most efficiently received by the B-pixel 73. The G-filter mainly transmits light having a medium-wavelength range 78. Green light belongs to the medium-wavelength range 78. For this reason, the reflected light and the like of the green light GL from the subject are most efficiently received by the G-pixel 72. Likewise, the R-filter mainly transmits light having a long-wavelength range 79. Red light belongs to the long-wavelength range 79. For this reason, the reflected light and the like of the red light RL from the subject are most efficiently received by the R-pixel 71.

However, each of the B-filter, the G-filter, and the R-filter has subsensitivity. Subsensitivity means sensitivity to light that has a wavelength range where light intends to be mainly received by a pixel including a color filter having another color (a wavelength range where the transmittance of a color filter having another color is high). The sensitivity of a color filter means that the color filter has a transmittance higher than 0. That is, the B-filter intends to mainly receive light belonging to the short-wavelength range 77, but transmits a part of light belonging to each of the medium-wavelength range 78 and the long-wavelength range 79 in addition to this. The G-filter intends to receive light belonging to the medium-wavelength range 78, but transmits a part of light belonging to each of the short-wavelength range 77 and the long-wavelength range 79. Likewise, the R-filter transmits a part of light belonging to each of the short-wavelength range 77 and the medium-wavelength range 78. For this reason, for example, in a case where the image of a subject is picked up using the narrow-band violet light Vn as illumination light in the special observation mode, the reflected light and the like of the narrow-band violet light Vn are received by the B-pixel 73. On the other hand, the G-pixel 72 and the R-pixel 71 also receive a part of the reflected light and the like of the narrow-band violet light Vn due to subsensitivity. Accordingly, in the special observation mode where the image of a subject is picked up using the narrow-band violet light Vn, a G-image of the subject picked up using the G-pixels 72 and an R-image of the subject picked up using the R-pixels 71 are obtained in addition to a B-image 91 (see FIG. 8) of the subject picked up using the B-pixels 73. Further, the G-image includes a subject image according to the subsensitivity of the G-filter. The same applies to the R-image.

A charge coupled device (CCD) sensor or a complementary metal oxide semiconductor (CMOS) sensor can be used as the image sensor 48. Further, the image sensor 48 of this embodiment is a primary color sensor, but a complementary color sensor can also be used as the image sensor 48. The complementary color sensor includes, for example, cyan pixels provided with cyan color filters, magenta pixels provided with magenta color filters, yellow pixels provided with yellow color filters, and green pixels provided with green color filters. In a case where the complementary color sensor is used, images obtained from the pixels having the respective colors can be converted into the B-image 91, the G-image, and the R-image by complementary color-primary color conversion. The same applies to a case where the primary color (RGB) sensor or the complementary color sensor includes one or more types of pixels having characteristics other than the above-mentioned characteristics, such as W pixels (white pixels that receive light having substantially the entire wavelength range).

The processor device 16 includes a controller 52, an image acquisition unit 54, an image processing unit 61, and a display controller 66 (see FIG. 2).

The controller 52 performs the overall control of the endoscope system 10, such as the synchronization control of the irradiation timing of illumination light and an image pickup timing. In a case where various types of settings are input using the console 19 or the like, the controller 52 inputs the setting to each part of the endoscope system 10, such as the light source controller 22, the image sensor 48, or the image processing unit 61.

The image acquisition unit 54 acquires the images of the subject picked up using the pixels having the respective colors, that is, RAW images from the image sensor 48. Further, the RAW images are images that are not yet subjected to demosaicing processing or complementary processing. In regard to the images not yet subjected to demosaicing processing or complementary processing, images acquired from the image sensor 48 and subjected to certain processing, such as noise reduction processing, are also included in the "RAW images". In this embodiment, the image acquisition unit 54 acquires the B-image 91, the G-image, and the R-image, that is, RAW images having three colors. Then, the image acquisition unit 54 generates an image for display or the like using these RAW images. In the following description, "an image for display or the like" output from the image acquisition unit 54 is referred to as an endoscopic image.

The image acquisition unit 54 comprises a digital signal processor (DSP) 56, a noise reduction section 58, and a conversion section 59 to perform various types of processing on the acquired RAW images as necessary and to generate an endoscopic image.

Figure 7:
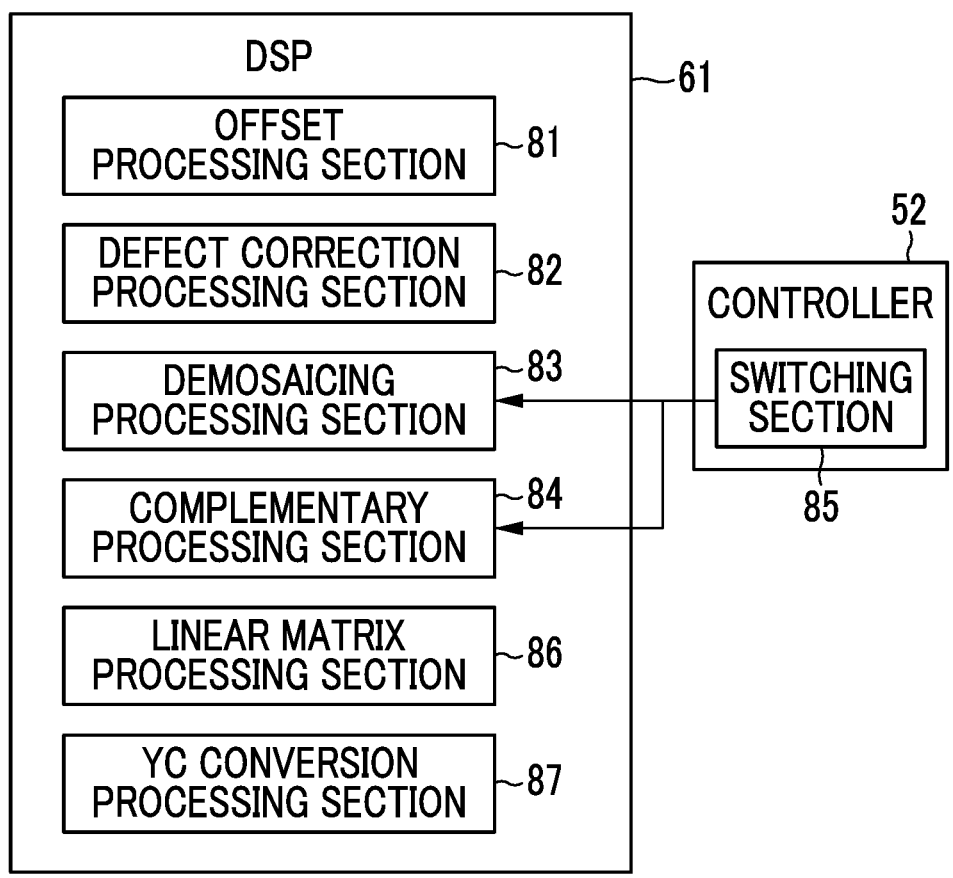
FIG. 7 is a block diagram illustrating the configuration of a DSP.

As shown in FIG. 7, the DSP 56 comprises, for example, an offset processing section 81, a defect correction processing section 82, a demosaicing processing section 83, a complementary processing section 84, a linear matrix processing section 86, and a YC conversion processing section 87. By using these sections, the DSP 56 performs various types of processing on the RAW images or an image that is generated using the RAW images.

The offset processing section 81 performs offset processing on the RAW images. The offset processing is processing for reducing dark current components from the RAW images and setting an accurate zero level. There is a case where the offset processing is referred to as clamp processing.

The defect correction processing section 82 performs defect correction processing on the RAW images. The defect correction processing is processing for correcting or generating the pixel value of a RAW pixel corresponding to a defective pixel of the image sensor 48 in a case where the image sensor 48 includes a pixel having a defect caused by a manufacturing process or a change with time.

Figure 8:
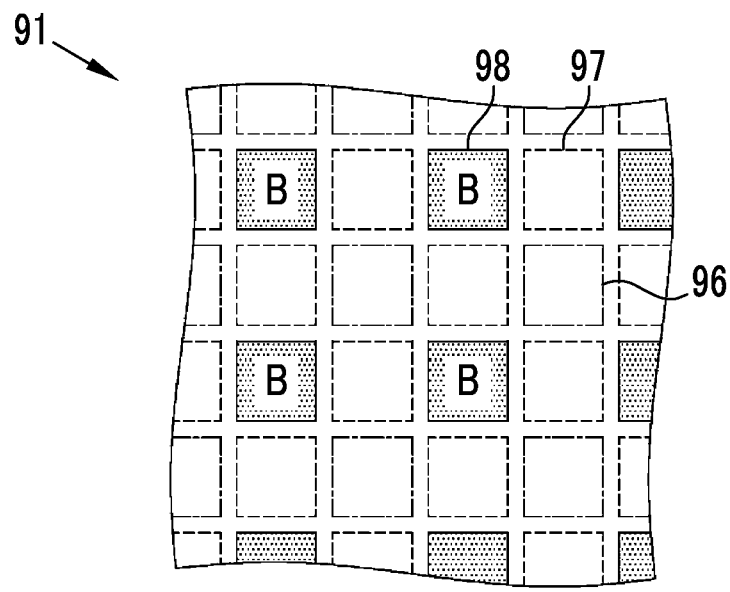
FIG. 8 is a diagram illustrating a RAW image.
Figure 9:
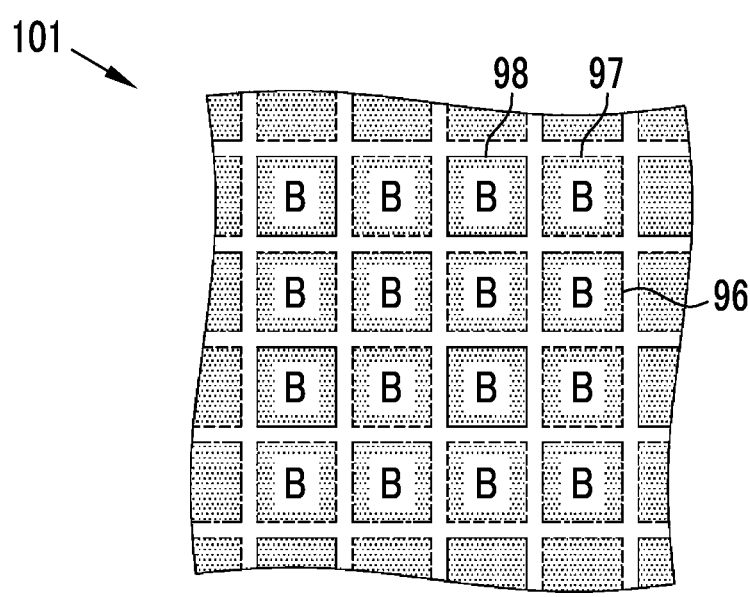
FIG. 9 is a diagram illustrating an image subjected to demosaicing processing.

The demosaicing processing section 83 performs demosaicing processing on the RAW images that have the respective colors and correspond to the color filters having the respective colors. The demosaicing processing is processing for generating a pixel value, which is missed in the RAW image due to the arrangement of the color filters, by interpolation. For example, as shown in FIG. 8, the B-image 91 has pixel values, which correspond to the amount of light received by the B-pixels 73 of the image sensor 48, at pixels 98 that are present at positions corresponding to the B-pixels 73 of the image sensor 48. On the other hand, the B-image 91 does not have pixel values at pixels 97 (pixels shown by a broken line. The same shall apply hereinafter.) that are present at positions corresponding to the G-pixels 72 of the image sensor 48. Likewise, the B-image 91 does not have pixel values at pixels 96 (pixels shown by a one-dot chain line. The same shall apply hereinafter.) that are present at positions corresponding to the R-pixels 71 of the image sensor 48. In a case where the demosaicing processing is performed on the B-image 91, the demosaicing processing section 83 generates the pixel values of the pixels 97 and 96 by interpolation that uses the pixel values of the pixels 98 present in the vicinity of each of the pixels 97 and 96. Accordingly, as shown in FIG. 9, a B-image 101 (the B-image subjected to the demosaicing processing) having pixel values, which correspond to the amount of light received by each B-pixel 73 of the image sensor 48, not only at the pixels 98 but also at the pixels 97 and 96 is generated. The contents of the demosaicing processing are the same even in the RAW images other than the B-image 91, that is, the G-image and the R-image.

There are a case where the demosaicing processing section 83 performs the demosaicing processing and a case where the demosaicing processing section 83 does not perform the demosaicing processing. The switching of whether to perform the demosaicing processing is controlled by a switching section 85 (see FIG. 7) of the controller 52. Specifically, the switching section 85 switches whether to perform demosaicing processing using "spectral information of illumination light" that is obtained in a case where the RAW images are picked up. The "spectral information of illumination light" is information according to the wavelength range of illumination light and/or the amount of light contributing to image pickup in each wavelength or each wavelength range. In this embodiment, the spectral information of illumination light includes the turn-on or turn-off of each color LED of the light source unit 20, such as the V-LED 20a, the amount of emitted light (including information about the length of emission time in addition to instantaneous emission intensity), and whether or not the optical filter is present, and the like. The switching section 85 obtains the spectral information of illumination light from the controller 52 or the light source controller 22.

The complementary processing section 84 performs complementary processing on the RAW images. The complementary processing is processing for complementing the pixel values of missing pixels of a specific color image using non-specific color images.

A "specific color" is one color of the color filters, which have the respective colors, of the image sensor 48. The "specific color image" is one of the RAW images that have the respective colors and correspond to the color filters having the respective colors. That is, the specific color image is one RAW image of the plurality of RAW images obtained from the image sensor 48. In this embodiment, the B-image 91, the G-image, or the R-image can be used as the specific color image. For example, the B-image 91, which is obtained in a case where the image of a subject is picked up using the narrow-band violet light Vn, is the specific color image.

A "non-specific color" is one color of the color filters except for the color filter having the specific color among the color filters, which have the respective colors, of the image sensor 48. The "non-specific color images" are any or all of the RAW images, which are different from the specific color image, of the RAW images having the respective colors. For example, in a case where the B-image 91, which is obtained in a case where the image of a subject is picked up using the narrow-band violet light Vn, is used as the specific color image, the G-image and the R-image except for the B-image 91 among three types of RAW images, that is, the B-image 91, the G-image, and the R-image are the non-specific color images.

The "missing pixel" means a pixel of which the pixel value is missed in the specific color image due to the arrangement of the color filters. For example, the missing pixels of the B-image 91 are the pixels 97 that are present at the positions of the G-pixels 72 of the image sensor 48 and the pixels 96 that are present at the positions of the R-pixels 71 of the image sensor 48 (see FIG. 8). The same applies to a case where the G-image or the R-image is used as the specific color image.

"Complementing" for a pixel value means supplying a pixel value without interpolation. Since processing performed by the complementary processing section 84 supplies missing pixel values of the specific color image using the pixel values of the non-specific color images without interpolation, the processing performed by the complementary processing section 84 is complementary processing.

The complementary processing section 84 complements the pixel values of the missing pixels of the specific color image using the pixel values of the non-specific color images to which gains are applied. "Gains are applied" means that addition, subtraction, multiplication, and division and other calculations are performed using predetermined gains. In this embodiment, the complementary processing section 84 multiplies the pixel values of the non-specific color images by the gains.

The gains used for the complementary processing are parameters of calculation for causing the pixel values of the non-specific color images to be close to the pixel values of the specific color image in a case where, for example, the image of a white subject is picked up. Coefficients for causing the received light spectra of pixels forming the pixel values of the specific color image and the received light spectra of pixels forming the pixel values of the non-specific color images to be close to each other are used as the gains in this embodiment. Specifically, the gains will be determined as follows.

Figure 10:
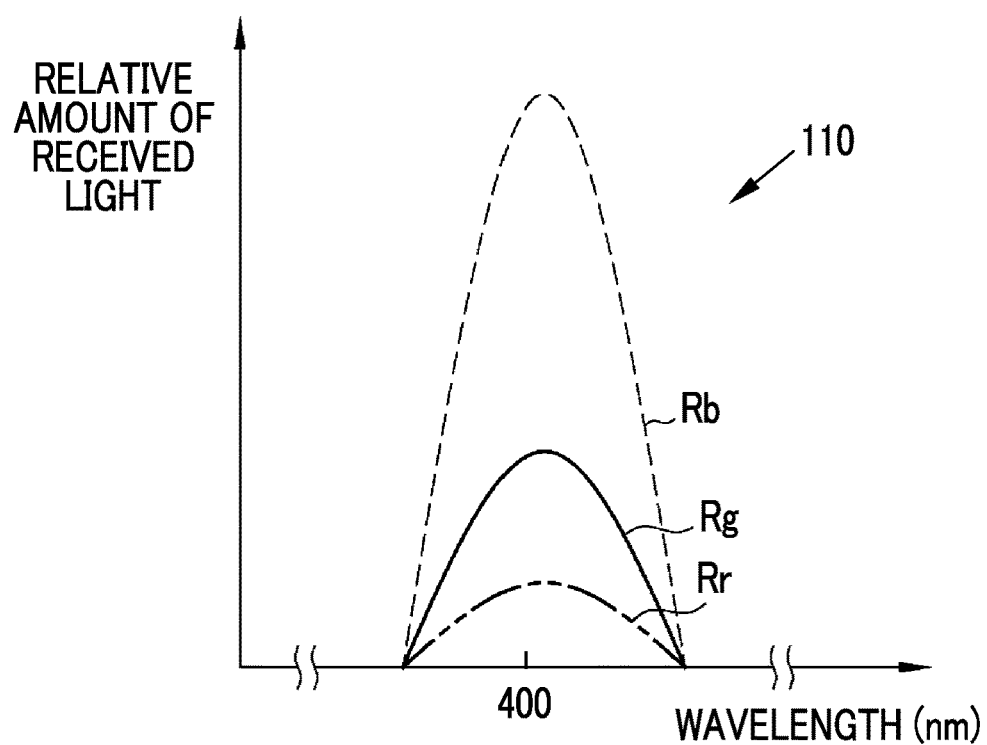
FIG. 10 is a graph showing a received light spectrum.

In the endoscope system 10, the spectral transmittance (see FIG. 6) of the color filters, which have the respective colors, of the image sensor 48 and the spectral information of illumination light used during image pickup are already known. Further, in a case where illumination light is narrow-band light, there is little influence of the reflectivity of a subject on a received light spectrum that is obtained by the color filter having each color. For this reason, a received light spectrum is simply obtained in advance using the spectral information of illumination light and the spectral transmittance of the color filter having each color, and gains are calculated from the calculated received light spectrum. For example, as shown in FIG. 10, a received light spectrum 110 is the product of the spectral information (see FIG. 4) of the narrow-band violet light Vn and the spectral transmittance (see FIG. 6) of the color filter having each color at each wavelength in a case where the narrow-band violet light Vn is used as illumination light. In this case, in a case where a received light spectrum Rb of the B-pixel 73, a received light spectrum Rg of the G-pixel 72, and a received light spectrum Rr of the R-pixel 71 are compared with each other, the peak of the received light spectrum Rg of the G-pixel 72 and the peak of the received light spectrum Rr of the R-pixel 71 are lower than the peak of the received light spectrum Rb of the B-pixel 73. The reason for this is that the G-pixel 72 and the R-pixel 71 receive the reflected light and the like of the narrow-band violet light Vn using the subsensitivity of the G-filter or the R-filter.

Figure 11:
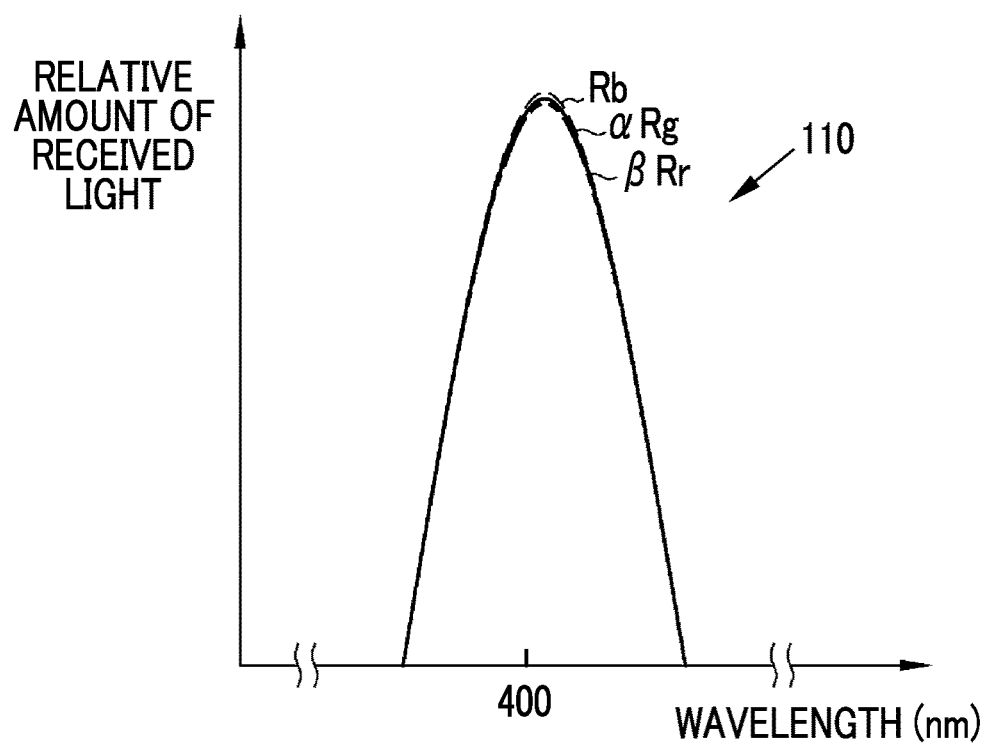
FIG. 11 is a graph showing the received light spectrum subjected to gain correction.

However, an interrelationship between the received light spectrum Rb of the B-pixel 73, the received light spectrum Rg of the G-pixel 72, and the received light spectrum Rr of the R-pixel 71 is constant. For example, as shown in FIG. 11, a received light spectrum $\alpha$Rg, which is $\alpha$ times the received light spectrum Rg of the G-pixel 72, substantially coincides with the received light spectrum Rb of the B-pixel 73 and a received light spectrum $\beta$Rr, which is $\beta$ times the received light spectrum Rr of the R-pixel 71, substantially coincides with the received light spectrum Rb of the B-pixel 73. For this purpose, the complementary processing section 84 uses the coefficient $\alpha$ and the coefficient $\beta$ as the gains in this embodiment.

Figure 12:
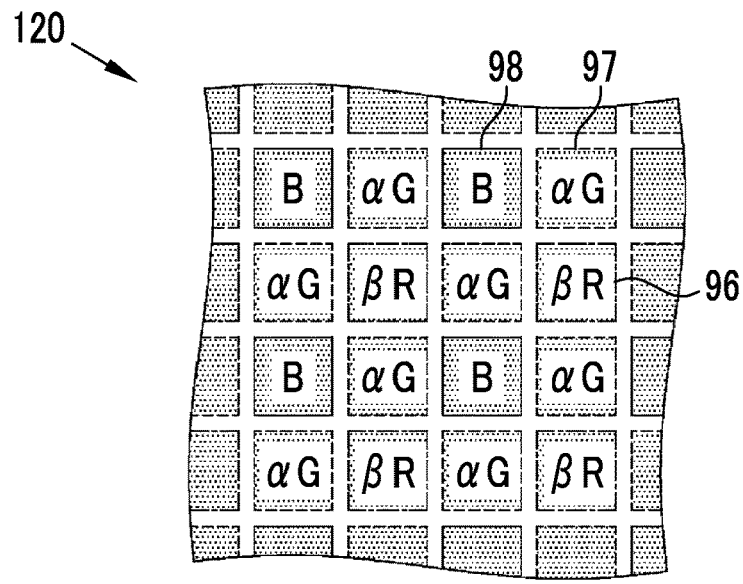
FIG. 12 is a diagram illustrating an image subjected to complementary processing (complemented specific color image).

Specifically, in a case where the B-image 91 obtained in a case where the image of a subject is picked up using the narrow-band violet light Vn is used as the specific color image, the complementary processing section 84 obtains a complemented B-image 120 as shown in FIG. 12 by supplying values, which are $\alpha$ times the pixel values of the G-image serving as the non-specific color image, to the pixels 97 of the B-image 91 and supplying values, which are $\beta$ times the pixel values of the R-image serving as the non-specific color image, to the pixels 96 of the B-image 91. The same applies to cases where the RAW images having the other colors are used as the specific color image. An image subjected to the complementary processing, such as the complemented B-image 120, is referred to as a complemented specific color image. The complemented specific color image is subjected to other processing as necessary, but is substantially an endoscopic image for display or the like.

In a case where illumination light is received by each pixel including a color filter having a specific color that is one of the color filters having the respective colors, the switching section 85 switches processing, which is to be performed, to the complementary processing. "Illumination light is received by each pixel including a color filter having a specific color" means that the image pickup of a subject using the reflected light and the like of illumination light is substantially performed by the pixels including the color filters having the specific color since substantially the entire wavelength range of illumination light is included in a wavelength range where the color filter having the specific color has main sensitivity (a wavelength range where the transmittance of the color filter having the specific color is higher than that of the color filter having the other color). That is, in a case where illumination light is monochromatic light, particularly, narrow-band light, the switching section 85 switches processing, which is to be performed, to the complementary processing. On the other hand, in a case where the wavelength range of illumination light is wider than a wavelength range having the main sensitivity of one color filter and the image of a subject is substantially picked up by the pixels having a plurality of colors, such as a case where illumination light is white light, the switching section 85 switches processing, which is to be performed, to the demosaicing processing.

The linear matrix processing section 86 performs linear matrix processing on an endoscopic image that is generated in a case where one or a plurality of RAW images are assigned to channels corresponding to the respective colors of R, G, and B. The linear matrix processing is processing for improving the color reproducibility of the endoscopic image. The linear matrix processing is performed in a case where the demosaicing processing is performed, and the linear matrix processing is not performed in a case where the complementary processing is performed.

The YC conversion processing section 87 performs processing for converting an endoscopic image, which is generated in a case where one or a plurality of RAW images are assigned to channels corresponding to the respective colors of R, G, and B, into an endoscopic image that includes a luminance channel Y, a color difference channel Cb, and a color difference channel Cr.

The noise reduction section 58 performs noise reduction processing on the endoscopic image, which includes the luminance channel Y, the color difference channel Cb, and the color difference channel Cr, using, for example, a moving-average method, a median filtering method, or the like. The conversion section 59 converts the endoscopic image, which includes the luminance channel Y, the color difference channel Cb, and the color difference channel Cr, which have been subjected to the noise reduction processing, into the endoscopic image that includes channels corresponding to the respective colors of B, G, and R, again.

The image processing unit 61 performs image processing, analysis processing, or the like on an endoscopic image, which is output from the image acquisition unit 54, as necessary. Further, the image processing unit 61 generates a special endoscopic image that shows the results of the image processing, the analysis processing, or the like, as necessary. The image processing performed by the image processing unit 61 is, for example, detection processing, emphasis processing, mask processing, or the like for an outline or the like. The analysis processing performed by the image processing unit 61 is calculation processing for biological information, such as oxygen saturation, extraction processing for a specific tissue or the like, determination processing for a symptom or the like, identification processing for identifying the stage of a cancer or the like, or the like. The special endoscopic image is, for example, an oxygen saturation image that shows oxygen saturation.

The display controller 66 converts the endoscopic image into a format suitable for display, and outputs the converted endoscopic image to the monitor 18. Accordingly, the monitor 18 displays the endoscopic image.

Figure 13:
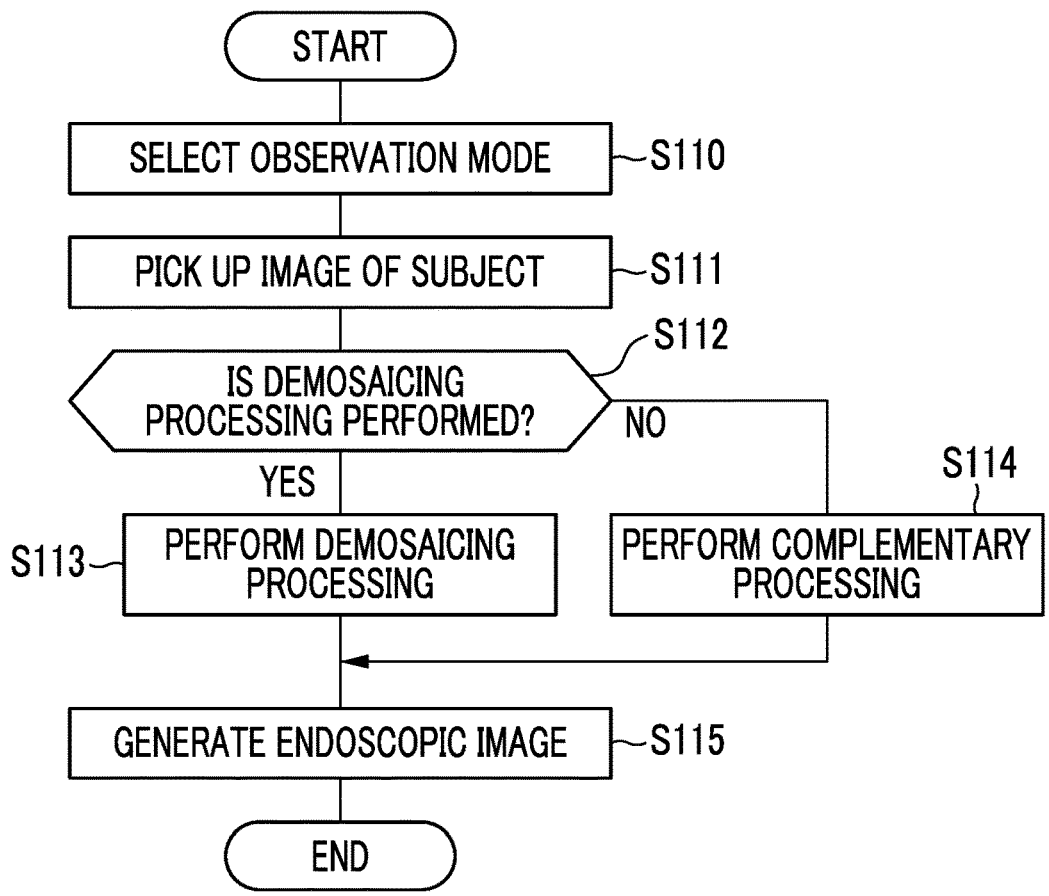
FIG. 13 is a flowchart showing a flow for generating an endoscopic image.

Hereinafter, the flow of an operation for generating an endoscopic image in the endoscope system 10 will be described with reference to a flowchart shown in FIG. 13. First, the observation mode is selected (set) (Step S110). Accordingly, the light source unit 20 emits illumination light required for the selected observation mode. Then, the image sensor 48 picks up the image of a subject using illumination light, which is emitted from the light source unit 20, automatically or on the basis of an image pickup instruction (Step S111).

In a case where the image sensor 48 picks up the image of the subject, the image acquisition unit 54 acquires RAW images from the image sensor 48 and generates an endoscopic image. In this case, the switching section 85 switches whether to perform demosaicing processing using the spectral information of the illumination light (Step S112). Specifically, in a case where the observation mode is the normal observation mode and the illumination light used during image pickup is white light (YES in Step S112), the switching section 85 switches processing, which is to be performed, to the demosaicing processing. For this reason, the demosaicing processing section 83 performs the demosaicing processing (Step S113) and generates the endoscopic image (Step S115). On the other hand, in a case where the observation mode is the special observation mode and the illumination light used during image pickup is narrow-band violet light Vn (NO in Step S112), the switching section 85 switches processing, which is to be performed, to the complementary processing. For this reason, the complementary processing section 84 performs the complementary processing (Step S114) and generates the endoscopic image (Step S115).

As described above, whether to perform the demosaicing processing is switched using the spectral information of the illumination light in a case where the endoscopic image is generated in the endoscope system 10. Since interpolation processing is included in a process for generating the endoscopic image that is generated through the demosaicing processing, the resolution of the endoscopic image is lower than the resolution of the RAW image. However, since whether to perform the demosaicing processing is switched as described above, the demosaicing processing can be adapted not to be performed in a case where it is not appropriate that the demosaicing processing is performed, such as a case where the same quality (resolution or the like) as the RAW image is required for the endoscopic image.

Further, in a case where the same resolution as the RAW image is required for the endoscopic image, the endoscope system 10 performs the complementary processing instead of the demosaicing processing and generates the endoscopic image (complemented specific color image). Since interpolation processing is not included in a process for generating the complemented specific color image, the complemented specific color image can maintain the same resolution as the RAW image. For this reason, in a case where it is not appropriate that the demosaicing processing is performed, the endoscope system 10 can generate a high-resolution complemented specific color image as an endoscopic image by performing the complementary processing.

Furthermore, in a case where the illumination light is received by each pixel including a color filter having a specific color, the switching section 85 switches processing, which is to be performed, to the complementary processing. The reason for this is that a case where monochromatic light, particularly, narrow-band light is used as the illumination light is substantially the same as a case where high resolution is required, such as a case where a thin blood vessel, a fine tissue, or the like is observed and a need to maintain the same resolution as the RAW image is particularly high in the endoscope system 10. For the same reason, it is preferable that the switching section 85 switches processing, which is to be performed, to the complementary processing in a case where the illumination light is violet light, blue light, or green light (that is, a case where substantially the entire wavelength range of the illumination light corresponds to light belonging to the short-wavelength range 77 or the medium-wavelength range 78), and it is particularly preferable that the switching section 85 switches processing, which is to be performed, to the complementary processing in a case where the illumination light is violet light or blue light (that is, substantially the entire wavelength range of the illumination light corresponds to light belonging to the short-wavelength range 77).

The endoscope system 10 according to the first embodiment can be an endoscope system comprising: the light source unit 20 that emits illumination light; the image sensor 48 that includes a color filter having one color for each pixel among color filters having a plurality of colors and picks up the image of a subject using the illumination light; and the complementary processing section 84 that performs complementary processing for complementing the pixel values of missing pixels of a specific color image, which is one of RAW images having the respective colors and corresponding to the color filters having the respective colors, using non-specific color images which are RAW images different from the specific color image.

Second Embodiment

In the first embodiment, the gains (the coefficient α and the coefficient β) used for the complementary processing are determined using the received light spectrum that is obtained from the spectral information of the illumination light and the spectral transmittance of the color filter having each color. However, it is preferable that the gains used for the complementary processing are determined in consideration of further the spectral reflectivity of a subject. The reason for this is that the resolution of the complemented specific color image can be maintained at a higher resolution depending on the width of the wavelength range of the illumination light in a case where the gains used for the complementary processing are determined in consideration of the spectral reflectivity of a living body.

Figure 14:
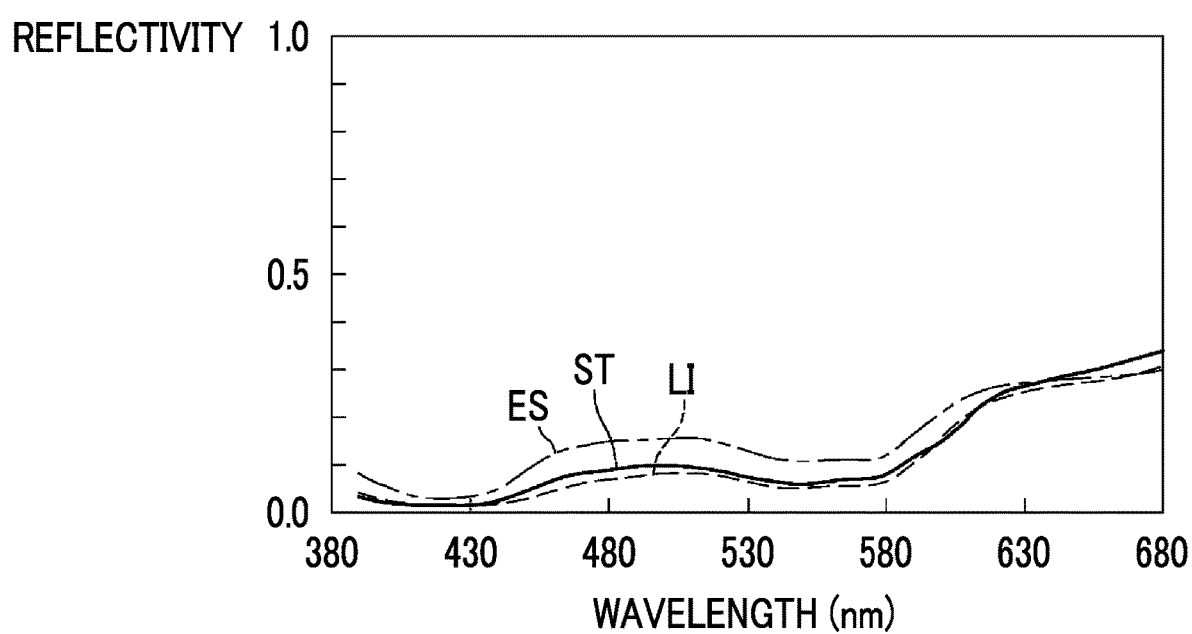
FIG. 14 is a graph showing the spectral reflectivities of the esophagus, the stomach, and the large intestine.
Figure 15:
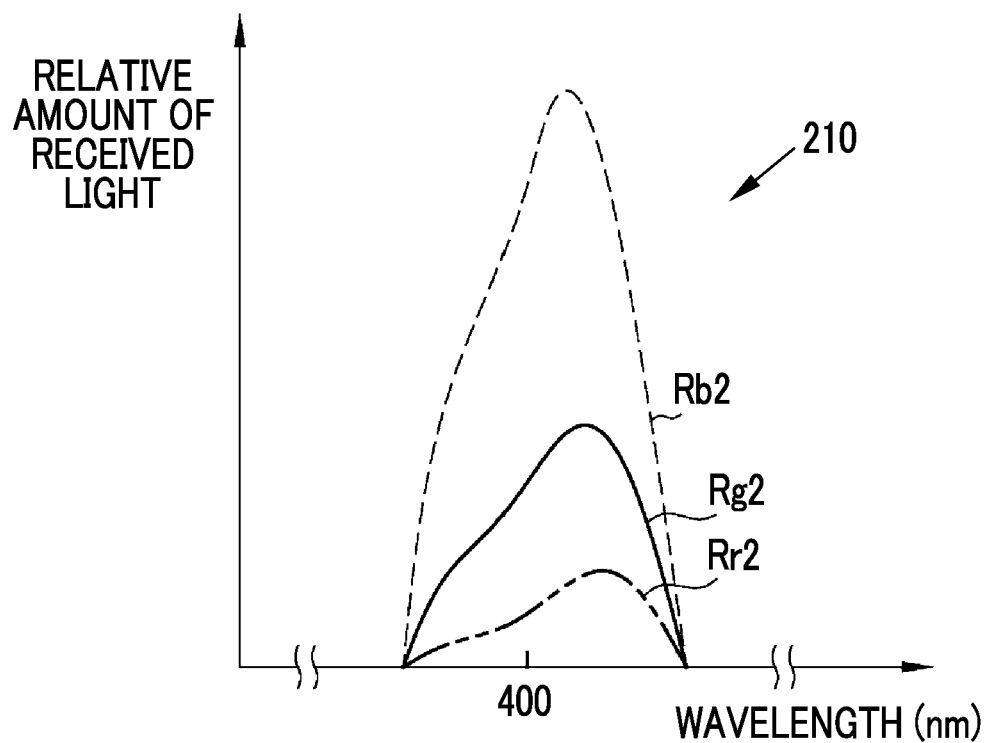
FIG. 15 is a graph showing a second received light spectrum.

For example, all the spectral reflectivity ES of the esophagus, the spectral reflectivity ST of the stomach, and the spectral reflectivity LI of the large intestine are not constant and are different from each other as shown in FIG. 14. That is, the spectral characteristics of a living body are not constant. Further, the spectral reflectivities differ depending on even a portion. For this reason, for example, as shown in FIG. 15, a second received light spectrum 210, which is obtained from the spectral information of illumination light, the spectral transmittance of the color filter having each color, and the spectral characteristics of a living body, is deformed as compared to the received light spectrum 110 (see FIG. 10) that is obtained without the consideration of the spectral reflectivity of the living body, depending on the width of the wavelength range of the illumination light.

Figure 16:
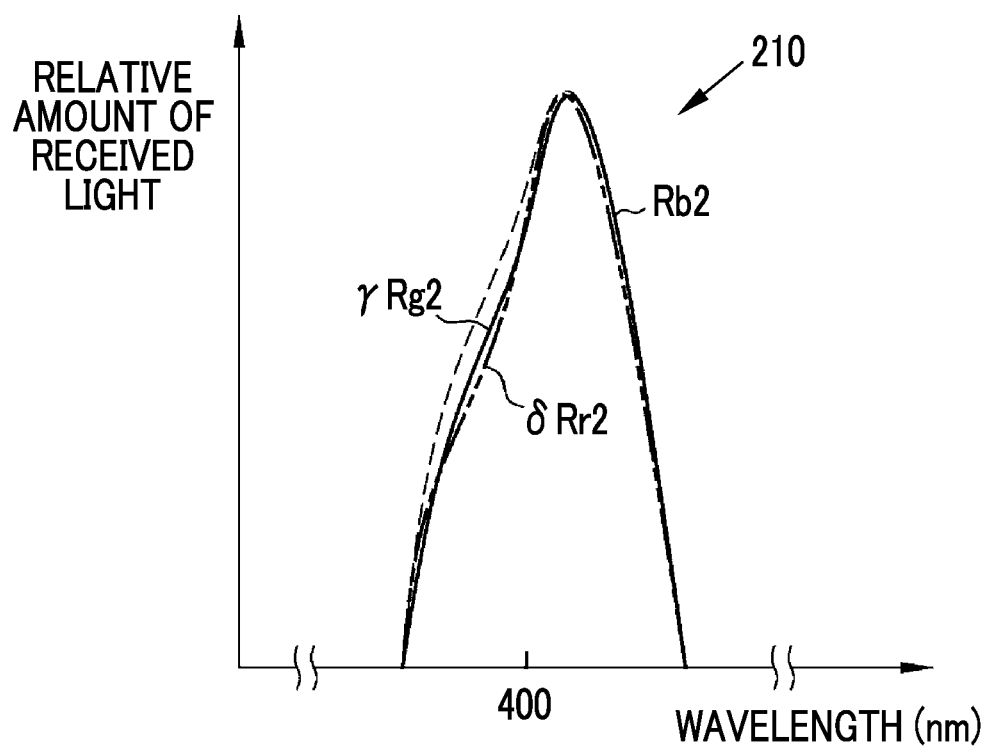
FIG. 16 is a graph showing the second received light spectrum subjected to gain correction.

For this reason, parameters (coefficients to be multiplied by pixel values, or the like) of calculation for causing the received light spectra of pixels forming the pixel values of the specific color image and the received light spectra of pixels forming the pixel values of the non-specific color images to be close to each other in the second received light spectrum 210 are used as the gains used for the complementary processing in this embodiment. For example, in a case where a received light spectrum γRg2, which is γ times a second received light spectrum Rg2 of the G-pixel 72, substantially coincides with a second received light spectrum Rb2 of the B-pixel 73 and a received light spectrum δRr2, which is δ times a second received light spectrum Rr2 of the R-pixel 71, substantially coincides with the second received light spectrum Rb2 of the B-pixel 73 as shown in FIG. 16, the complementary processing section 84 uses the coefficient γ and the coefficient δ as the gains instead of the coefficient α and the coefficient β of the first embodiment.

Figure 17:
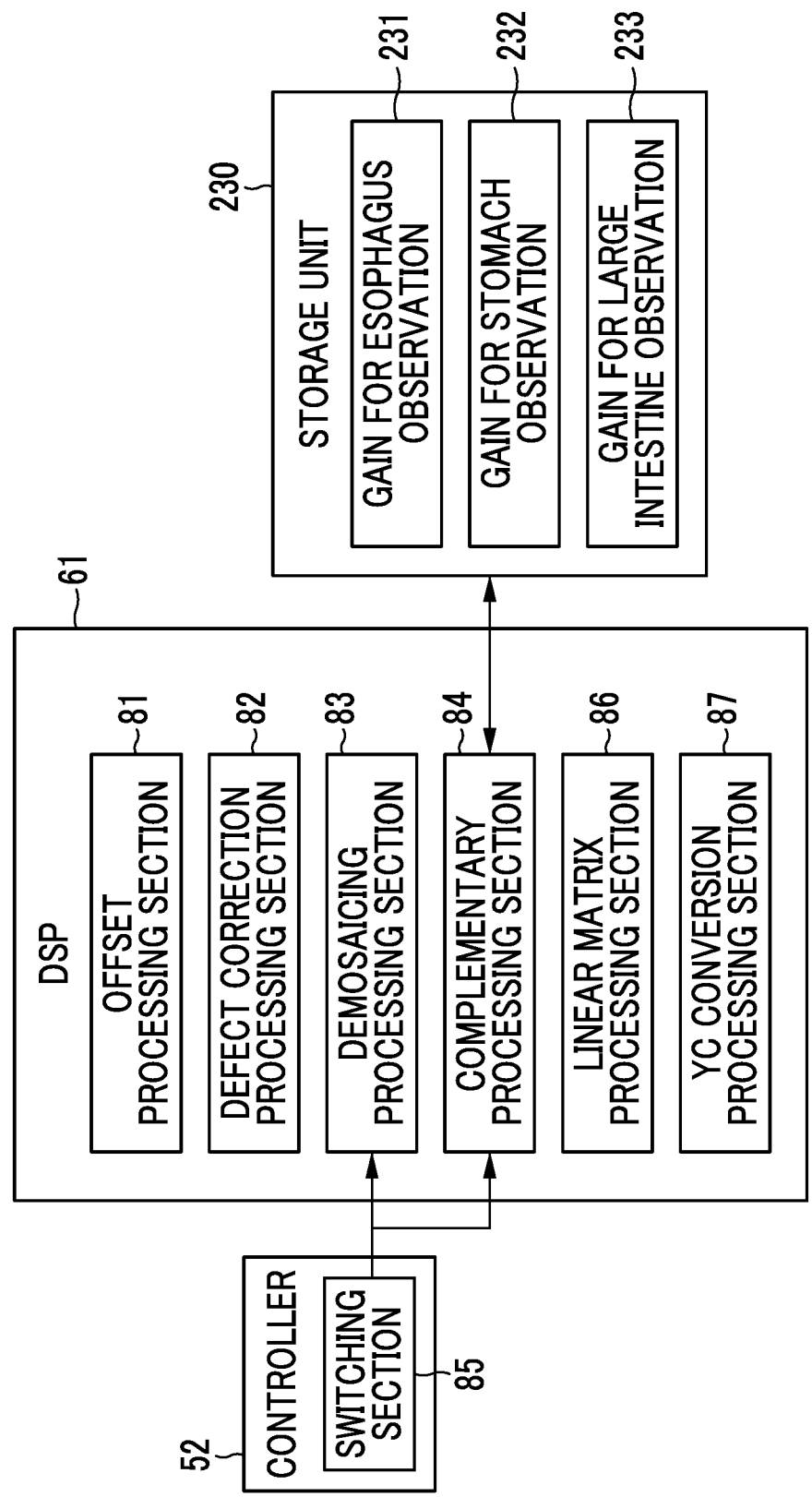
FIG. 17 is a block diagram showing a part of the configuration of a processor device of a modification example.

In a case where the spectral characteristics of a living body are considered as described above, it is preferable that the processor device 16 is provided with a storage unit 230 storing gains used for the complementary processing for each portion of a subject as shown in FIG. 17. The storage unit 230 stores, for example, gains 231 for esophagus observation, gains 232 for stomach observation, and gains 233 for large intestine observation. Further, it is preferable that the complementary processing section 84 switches gains to be used for each portion of the subject according to the setting of a portion to be observed or any switching operation. For example, in a case where the portion to be observed is the stomach, the complementary processing section 84 reads out the gains 232 for stomach observation from the storage unit 230 automatically or through manual selection and uses the gains 232 for stomach observation in the complementary processing.

In a case where gains for each portion to be observed are stored in advance and gains to be used are adapted to be switched according to a portion to be observed as described above, more accurate complementary processing can be performed so as to correspond to the spectral characteristics of each portion to be observed. As a result, the complemented specific color image can maintain higher resolution depending on the width of the wavelength range of the illumination light.

In a case where the illumination light is narrow-band light and the wavelength range of the illumination light is sufficiently narrow, it is preferable that the gains used for the complementary processing are determined without the consideration of the spectral reflectivity of the living body as in the first embodiment. The reason for this is that the influence of the spectral reflectivity of the living body can often be substantially ignored. Further, the reason for this is that the complemented specific color image can often be maintained at a higher resolution in a case where the illumination light is narrow-band light and the gains used for the complementary processing are determined without the consideration of the spectral reflectivity of the living body since the spectral reflectivity of the living body has an error caused by the individual difference or the like of the living body.

Figure 18:
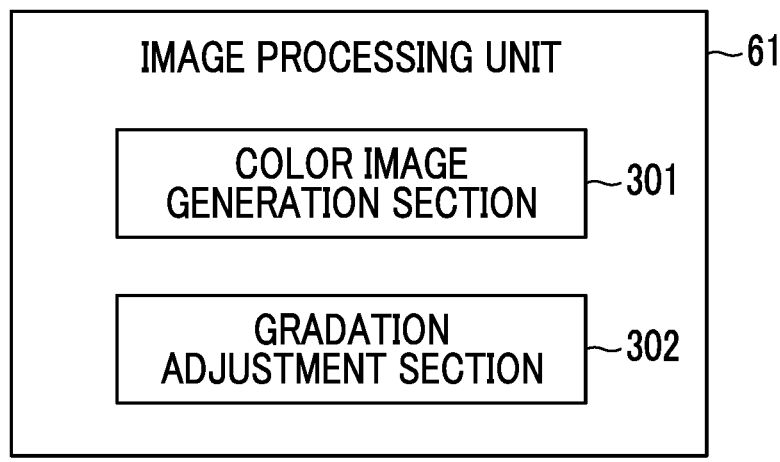
FIG. 18 is a block diagram showing the configuration of an image processing unit.

The complemented specific color images of the first and second embodiments are monochrome images, but a color image can be generated using the complemented specific color image. In this case, the image processing unit 61 is provided with a color image generation section 301 and a gradation adjustment section 302 as shown in FIG. 18.

Figure 19:
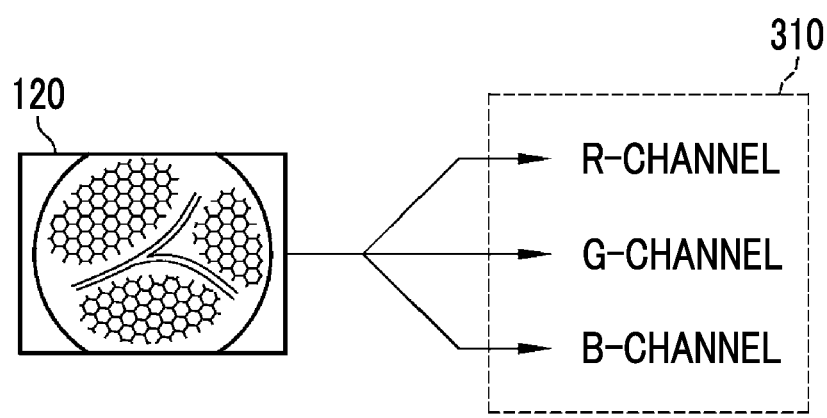
FIG. 19 is a diagram illustrating the action of the image processing unit.

As shown in FIG. 19, the color image generation section 301 generates a color image 310 by assigning the complemented specific color image, such as the complemented B-image 120, to color channels corresponding to the respective colors of R, G, and B. Then, the gradation adjustment section 302 performs gradation adjustment processing in a case where the complemented specific color image is assigned to the respective color channels or on the color image 310 where the complemented specific color image is assigned to the respective color channels.

Figure 20:
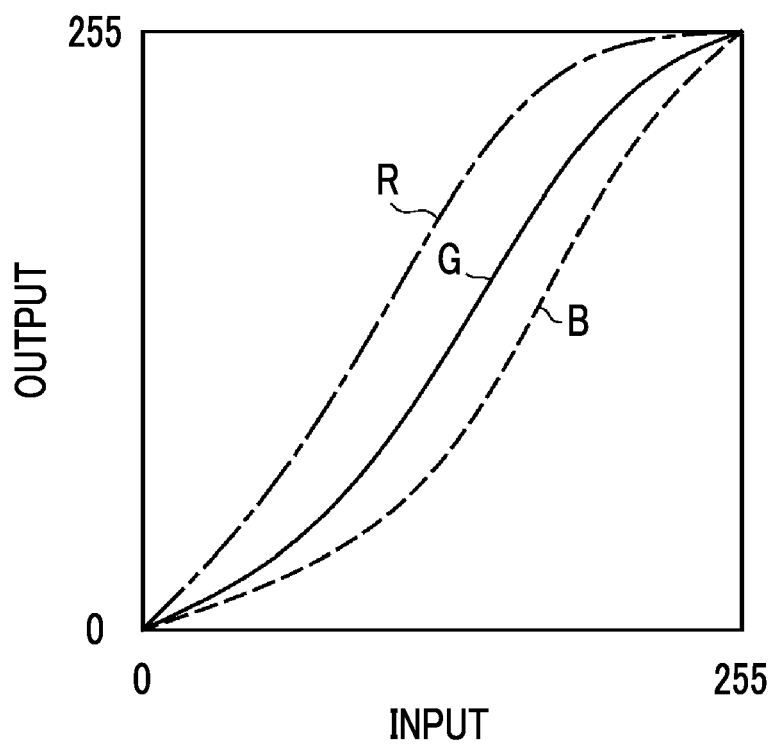
FIG. 20 is a tone curve that is used for gradation adjustment for making a natural tone.
Figure 21:
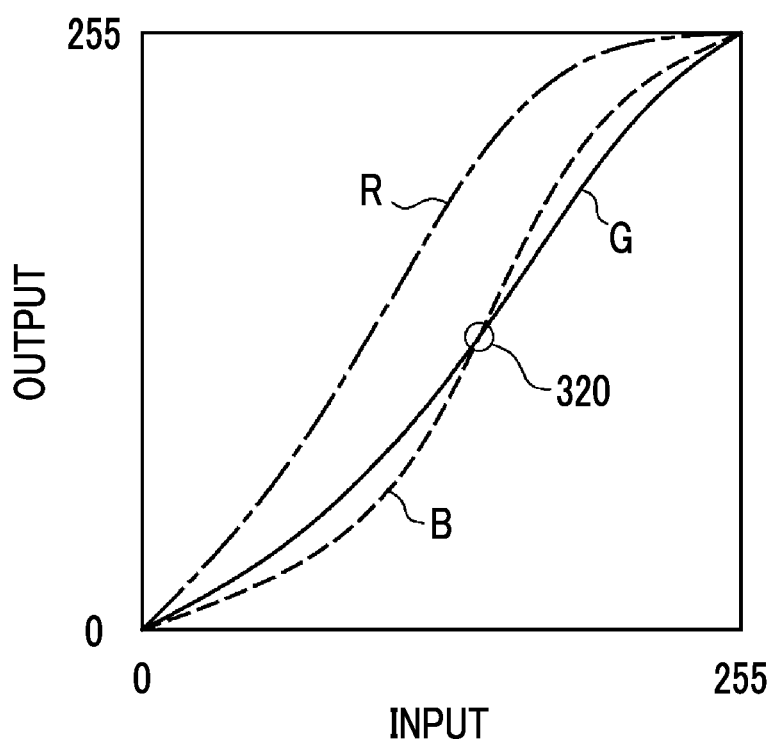
FIG. 21 is a tone curve that is used for gradation adjustment for making a natural tone.

For example, in a case where the gradation adjustment section 302 performs gradation adjustment according to a tone curve corresponding to a balance of substantially "R>G>B" as shown in FIG. 20, a color image 310 having a tone close to a so-called white light image, which is picked up using white light, can be obtained. Further, as shown in FIG. 21, a tone curve for a G-channel and a tone curve for a B-channel are caused to have an intersection 320, a balance of substantially "R>G>B" is set in a range where an input pixel value is small, and a balance of substantially "R>B>G" is set in a range where an input pixel value is large. In this case, the reddishness of a specific tissue, such as a blood vessel, which is likely to absorb illumination light, is increased. For this reason, the visibility of a specific tissue, such as a blood vessel, can be improved as compared to a white light image while high resolution equivalent to a RAW image is maintained.

Figure 22:
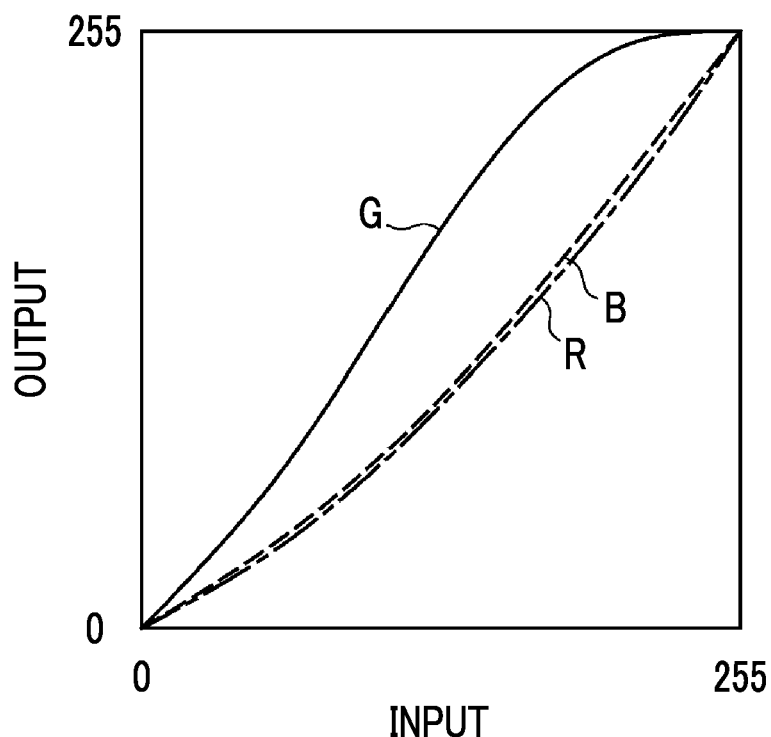
FIG. 22 is a tone curve that is used for gradation adjustment for changing a mucous membrane into a greenish color.
Figure 23:
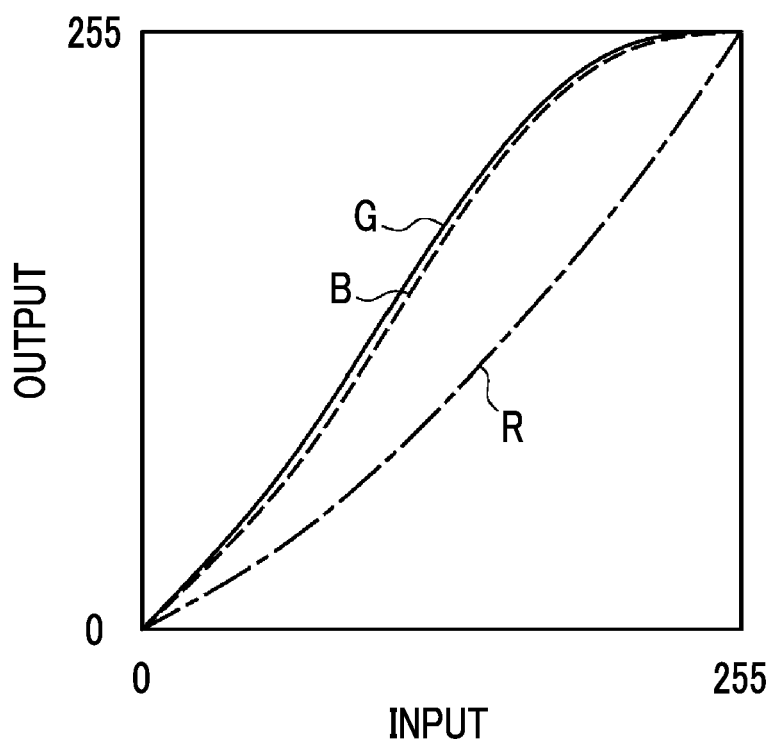
FIG. 23 is a tone curve that is used for gradation adjustment for changing a mucous membrane into a cyan color.

Further, in a case where the gradation adjustment section 302 performs gradation adjustment according to a tone curve corresponding to a balance of substantially "G>R≈R" as shown in FIG. 22, a color image 310 where a mucous membrane has a greenish color can be obtained. Likewise, in a case where the gradation adjustment section 302 performs gradation adjustment according to a tone curve corresponding to a balance of substantially "B≈G>R" as shown in FIG. 23, a color image 310 where a mucous membrane has a cyan color can be obtained. These can increase a distance between the color of a bright tissue, such as a mucous membrane, and the color of a dark tissue, such as a blood vessel, in L*a*b* color space. For this reason, a color image 310 where, for example, the visibility of a blood vessel with respect to a mucous membrane is good can be generated.

Figure 24:
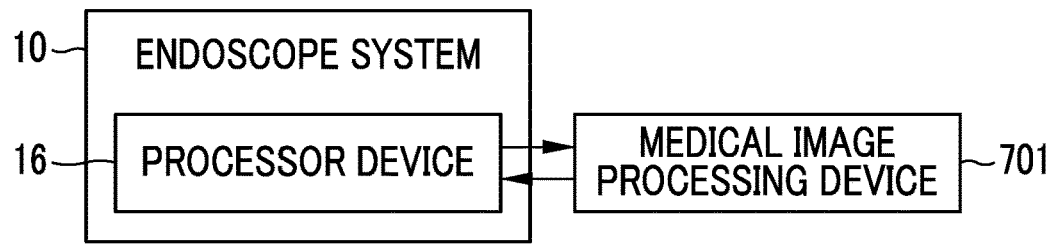
FIG. 24 is a diagram illustrating a relationship between the endoscope system and an image processing device.
Figure 25:
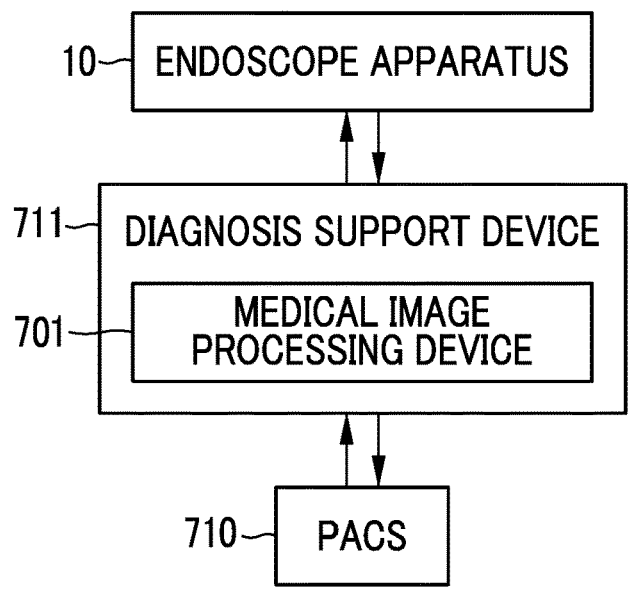
FIG. 25 is a diagram illustrating a relationship between the endoscope system and PACS and a diagnosis support device.
Figure 26:
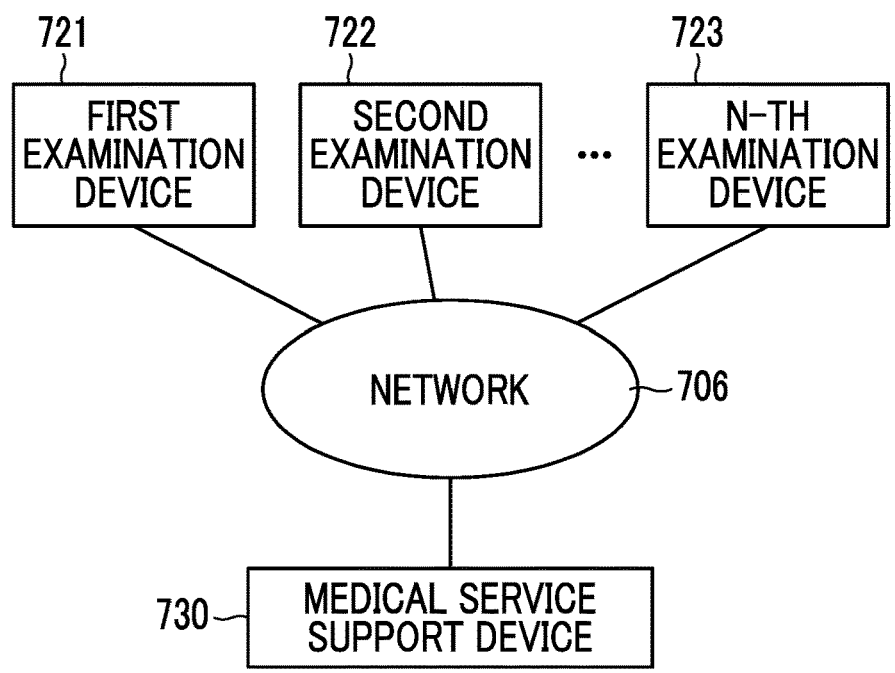
FIG. 26 is a diagram illustrating a relationship between various examination devices and a medical service support device.

In addition, some or all of the respective sections of the image processing unit 61 and/or the DSP 56 of the endoscope system 10 can be provided in, for example, a medical image processing device 701 that communicates with the processor device 16 and is connected to the endoscope system 10 as shown in FIG. 24. Further, as shown in FIG. 25, some or all of the respective sections of the image processing unit 61 and/or the DSP 56 of the endoscope system 10 can be provided in, for example, a diagnosis support device 711 acquiring a RAW image, which is picked up by the endoscope 12, directly from the endoscope system 10 or indirectly from a picture archiving and communication system (PACS) 710. Furthermore, as shown in FIG. 26, some or all of the respective sections of the image processing units 61 and/or the DSPs 56 of the endoscope systems 10 can be provided in a medical service support device 730 that is connected to various examination devices, such as a first examination device 721, a second examination device 722, . . . and an N-th examination device 723, each of which includes the endoscope system 10, through a network 726.

Further, a capsule endoscope can be used as the endoscope 12. In this case, the light source device 14 and a part of the processor device 16 can be mounted on the capsule endoscope.

In the respective embodiments and the modification example, the hardware structures of processing units for performing various types of processing, such as the light source controller 22, the controller 52, the image acquisition unit 54, the image processing unit 61, and the display controller 66, are various processors to be described below. The various processors include: a central processing unit (CPU) that is a general-purpose processor functioning as various processing units by executing software (program); a programmable logic device (PLD) that is a processor of which circuit configuration can be changed after manufacture, such as a field programmable gate array (FPGA); a dedicated electrical circuit that is a processor having circuit configuration designed exclusively to perform various kinds of processing; and the like.

One processing unit may be formed of one of these various processors, or may be formed of a combination of two or more same kind or different kinds of processors (for example, a plurality of FPGAs or a combination of a CPU and an FPGA). Further, a plurality of processing units may be formed of one processor. As an example where a plurality of processing units are formed of one processor, first, there is an aspect where one processor is formed of a combination of one or more CPUs and software as typified by a computer, such as a client or a server, and functions as a plurality of processing units. Second, there is an aspect where a processor fulfilling the functions of the entire system, which includes a plurality of processing units, by one integrated circuit (IC) chip as typified by System On Chip (SoC) or the like is used. In this way, various processing units are formed using one or more of the above-mentioned various processors as hardware structures.

In addition, the hardware structures of these various processors are more specifically electrical circuitry where circuit elements, such as semiconductor elements, are combined.

EXPLANATION OF REFERENCES

10: endoscope system
12: endoscope
12a: insertion part
12b: operation part
12c: bendable part
12d: distal end part
12e: angle knob
13a: zoom operation part
13b: mode switching operation part
14: light source device
16: processor device
18: monitor
19: console
20: light source unit
22: light source controller
30a: illumination optical system
30b: image pickup optical system
45: illumination lens
46: objective lens
47: zoom lens
48: image sensor
52: controller
54: image acquisition unit
56: digital signal processor (DSP)
58: noise reduction section
59: conversion section
61: image processing unit
66: display controller
71: R-pixel
72: G-pixel
73: B-pixel
77: short-wavelength range
78: medium-wavelength range
79: long-wavelength range
81: offset processing section
82: defect correction processing section
83: demosaicing processing section
84: complementary processing section
85: switching section
86: linear matrix processing section
87: YC conversion processing section
91: B-image
96: pixel present at position corresponding to R-pixel of image sensor
97: pixel present at position corresponding to G-pixel of image sensor
98: pixel present at position corresponding to B-pixel of image sensor
101: B-image subjected to demosaicing processing
110: received light spectrum
120: complemented B-image
210: second received light spectrum
230: storage unit
231: gain for esophagus observation
232: gain for stomach observation
233: gain for large intestine observation
301: color image generation section 302: gradation adjustment section
310: color image
320: intersection
701: medical image processing device
710: PACS
711: diagnosis support device
721: first examination device
722: second examination device
723: N-th examination device
726: network
730: medical service support device
B: blue color filter
G: green color filter
R: red color filter
VL: violet light
BL: blue light
GL: green light
RL: red light
Vn: narrow-band violet light
Y: luminance channel
Cb: color difference channel
Cr: color difference channel
Rb: received light spectrum of B-pixel
Rg: received light spectrum of G-pixel
Rr: received light spectrum of R-pixel
ES: spectral reflectivity of esophagus
LI: spectral reflectivity of large intestine
ST: spectral reflectivity of stomach
Rb2: second received light spectrum of B-pixel
Rg2: second received light spectrum of G-pixel
Rr2: second received light spectrum of R-pixel
S110, S111, S112, S113, S114, S115: step of operation

What is claimed is:

1. An endoscope system comprising:
a light source that emits illumination light;
an image sensor that includes a color filter having one color for each pixel among color filters having a plurality of colors and picks up an image of a subject using the illumination light; and
a processor configured to
  perform demosaicing processing on RAW images having the respective colors and corresponding to the color filters having the respective colors, and
  perform complementary processing for complementing a pixel value of a missing pixel of a specific color image, which is one of the RAW images having the respective colors and corresponding to the color filters having the respective colors, using a non-specific color image which is a RAW image different from the specific color image,
wherein the processor switches processing to be performed between the demosaicing processing and the complementary processing using spectral information of the illumination light.

2. The endoscope system according to claim 1, the processor further configured to
perform complementary processing for complementing a pixel value of a missing pixel of a specific color image, which is one of the RAW images having the respective colors and corresponding to the color filters having the respective colors, using a non-specific color image which is a RAW image different from the specific color image,
wherein the processor switches processing to be performed to the complementary processing in a case where the illumination light is at least one of monochromatic light or narrow-band light corresponding to the color filters having the respective colors as the spectral information.

3. The endoscope system according to claim 1, wherein the processor complements the pixel value of the missing pixel of the specific color image using pixel values of the non-specific color image multiplied by gains.

4. The endoscope system according to claim 2, wherein the processor complements the pixel value of the missing pixel of the specific color image using pixel values of the non-specific color image multiplied by gains.

5. The endoscope system according to claim 3, wherein the gains are parameters of calculation for causing the pixel values of the non-specific color image to be close to pixel values of the specific color image in a case where an image of a white subject is picked up.

6. The endoscope system according to claim 4, wherein the gains are parameters of calculation for causing the pixel values of the non-specific color image to be close to pixel values of the specific color image in a case where an image of a white subject is picked up.

7. The endoscope system according to claim 3, wherein the gains are coefficients for causing received light spectra of pixels forming pixel values of the specific color image and received light spectra of pixels forming the pixel values of the non-specific color image to be close to each other in a first received light spectrum that is obtained from spectral information of the illumination light and spectral transmittance of the color filters.

8. The endoscope system according to claim 4, wherein the gains are coefficients for causing received light spectra of pixels forming pixel values of the specific color image and received light spectra of pixels forming the pixel values of the non-specific color image to be close to each other in a first received light spectrum that is obtained from spectral information of the illumination light and spectral transmittance of the color filters.

9. The endoscope system according to claim 3, wherein the gains are coefficients for causing received light spectra of pixels forming pixel values of the specific color image and received light spectra of pixels forming the pixel values of the non-specific color image to be close to each other in a second received light spectrum that is obtained from spectral information of the illumination light, spectral transmittance of the color filters, and spectral characteristics of the subject.

10. The endoscope system according to claim 4, wherein the gains are coefficients for causing received light spectra of pixels forming pixel values of the specific color image and received light spectra of pixels forming the pixel values of the non-specific color image to be close to each other in a second received light spectrum that is obtained from spectral information of the illumination light, spectral transmittance of the color filters, and spectral characteristics of the subject.

11. The endoscope system according to claim 5, wherein the gains are coefficients for causing received light spectra of pixels forming pixel values of the specific color image and received light spectra of pixels forming the pixel values of the non-specific color image to be close to each other in a second received light spectrum that is obtained from spectral information of the illumination light, spectral transmittance of the color filters, and spectral characteristics of the subject.

12. The endoscope system according to claim 9, further comprising:
a storage unit that stores the gains for each portion of the subject,
wherein the processor switches the gains to be used for each portion of the subject on the basis of the gains stored in the storage unit.

13. The endoscope system according to claim 1,
wherein the illumination light is narrow-band light.

14. The endoscope system according to claim 2,
wherein the illumination light is narrow-band light.

15. The endoscope system according to claim 3,
wherein the illumination light is narrow-band light.

16. The endoscope system according to claim 13,
wherein the narrow-band light is at least one of violet light, blue light, or green light.

17. The endoscope system according to claim 1, the processor further configured to:
generate a color image using a complemented image.

18. The endoscope system according to claim 2, the processor further configured to:
generate a color image using a complemented image.

19. The endoscope system according to claim 3, the processor further configured to:
generate a color image using a complemented image.

20. An endoscope system comprising:
a light source that emits illumination light;
an image sensor that includes a color filter having one color for each pixel among color filters having a plurality of colors and picks up an image of a subject using the illumination light; and
a processor configured to
perform demosaicing processing on RAW images having the respective colors and corresponding to the color filters having the respective colors, and
perform complementary processing for complementing a pixel value of a missing pixel of a specific color image, which is one of the RAW images having the respective colors and corresponding to the color filters having the respective colors, using a non-specific color image which is a RAW image different from the specific color image,
wherein the processor switches processing to be performed to the complementary processing in a case where the illumination light is at least one of monochromatic light or narrow-band light corresponding to the color filters having the respective colors using spectral information of the illumination light.

* * * * *